(12) United States Patent
Gura et al.

(10) Patent No.: US 8,034,161 B2
(45) Date of Patent: Oct. 11, 2011

(54) CARBON DIOXIDE GAS REMOVAL FROM A FLUID CIRCUIT OF A DIALYSIS DEVICE

(75) Inventors: Victor Gura, Beverly Hills, CA (US); Carlos Jacobo Ezon, Woodland Hills, CA (US); Masoud Beizai, Laguna Hills, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 377 days.

(21) Appl. No.: 12/355,128

(22) Filed: Jan. 16, 2009

(65) Prior Publication Data

US 2009/0282980 A1    Nov. 19, 2009

Related U.S. Application Data

(60) Provisional application No. 61/021,965, filed on Jan. 18, 2008.

(51) Int. Cl.
*B01D 53/22* (2006.01)
*B01D 19/00* (2006.01)

(52) U.S. Cl. .............. 95/46; 95/45; 95/51; 96/6; 96/8; 96/9; 210/640; 210/645; 210/321.6; 210/321.75; 210/321.87; 604/4.01; 422/44

(58) Field of Classification Search .......... 96/4, 6, 96/8, 9, 10; 95/45, 46, 51; 210/640, 645, 210/321.6, 321.75, 321.87; 422/44; 604/4.01
See application file for complete search history.

(56) References Cited

U.S. PATENT DOCUMENTS

| | | | |
|---|---|---|---|
| 4,213,859 A * | 7/1980 | Smakman et al. | 210/638 |
| 4,302,223 A * | 11/1981 | Booth et al. | 96/6 |
| 4,345,999 A * | 8/1982 | Sigdell et al. | 96/6 |
| 4,879,041 A * | 11/1989 | Kurokawa et al. | 95/46 |
| 6,746,514 B2 * | 6/2004 | Bedingfield et al. | 95/46 |
| 6,773,670 B2 * | 8/2004 | Stringer et al. | 96/6 |
| 6,860,922 B2 * | 3/2005 | Watari et al. | 96/6 |
| 6,960,179 B2 | 11/2005 | Gura | |
| 7,309,323 B2 | 12/2007 | Gura et al. | |
| 7,621,982 B2 * | 11/2009 | Kang et al. | 96/4 |
| 7,645,253 B2 | 1/2010 | Gura et al. | |
| 7,854,718 B2 | 12/2010 | Gura et al. | |
| 2005/0150832 A1 * | 7/2005 | Tsukamoto | 210/638 |
| 2006/0090645 A1 * | 5/2006 | Kent | 95/46 |
| 2006/0241543 A1 | 10/2006 | Gura | |
| 2009/0076434 A1 | 3/2009 | Mischelevich et al. | |
| 2009/0101552 A1 | 4/2009 | Fulkerson et al. | |
| 2009/0101577 A1 | 4/2009 | Fulkerson et al. | |
| 2009/0114037 A1 | 5/2009 | Smith | |
| 2009/0120864 A1 | 5/2009 | Fulkerson et al. | |
| 2009/0173682 A1 | 7/2009 | Robinson et al. | |
| 2009/0282980 A1 | 11/2009 | Gura et al. | |

FOREIGN PATENT DOCUMENTS

WO    WO 2007/019519 A2    2/2007

\* cited by examiner

*Primary Examiner* — Jason M Greene

(74) *Attorney, Agent, or Firm* — Hamilton, Brook, Smith & Reynolds, P.C.

(57) ABSTRACT

The present invention is directed to degassing devices for dialysate circuits. One embodiment has a first housing and a second housing positioned within the first housing in an annular relationship. A second embodiment comprises a dialysate regeneration system with urease, a dialyzer, and a housing with an external wall, where the external wall is exposed to atmosphere and comprises a material that passes gas but does not pass liquid and where the housing is positioned between the urease and dialyzer.

11 Claims, 3 Drawing Sheets

US 8,034,161 B2

CARBON DIOXIDE GAS REMOVAL FROM A FLUID CIRCUIT OF A DIALYSIS DEVICE

CROSS-REFERENCE

The present application relies on U.S. Provisional Application No. 61/021,965, filed on Jan. 18, 2008, for priority and is herein incorporated by reference.

FIELD OF THE INVENTION

The present invention generally relates to the field of hemodialysis, and more specifically to a method and system of efficiently removing carbon dioxide, or any gas, from the dialysate circuit of a dialysis system without compromising the solute-removal performance of a hemodialysis device.

BACKGROUND OF THE INVENTION

Closed loop multi-pass sorbent based hemodialyzers have the advantage of being portable and compact while being able to regenerate dialysate using a plurality of sorbents. Typically these sorbents are used in disposable cartridges/canisters and comprise sorbent composition layers similar to those used in prior systems, such as urease, zirconium phosphate, hydrous zirconium oxide and activated carbon. As spent dialysate comprising urea, diffused from impure blood in the dialyzer, passes through prior art sorbent cartridges, carbon dioxide and ammonia are produced as two unwanted byproducts of the chemical reactions. While ammonia is adsorbed in zirconium-based cartridges, carbon dioxide is not captured, mixes in the dialysate, and manifests as carbon dioxide bubbles in the dialysate circuit. Large amounts of carbon dioxide leave the liquid phase and interfere with the smooth pumping of dialysate. In addition other dissolved gases may exit from the liquid phase during processing adding to the volume of gas in the system.

Accordingly, there is a need for a degassing device that can remove unwanted carbon dioxide, and other gases, from the dialysate circuit. The degassing device needs to be particularly suitable for a portable hemodialyzer, where the orientation of the dialyzer should not disrupt or degrade the efficiency of the degassing device. At the same time, the degassing device needs to be small in size, light and low cost so that it can be a disposable component.

SUMMARY OF THE INVENTION

It is an object of the present invention to provide a degassing device that efficiently vents or removes carbon-dioxide, and other gas, bubbles, from dialysate circuit, that are produced from urea split by urease in the sorbent system of a dialysis device.

It is also an object of the present invention to have a degassing device that is particularly suitable for a portable hemodialyzer, such as one configured as a portable artificial kidney (PAK), where the orientation of the dialyzer should not disrupt or degrade the efficiency of the degassing device.

Accordingly, it is another object of the present invention the degassing device needs to be small in size, light and low cost so that it can be a disposable component.

In one embodiment, the degassing device of the present invention comprises two annular concentric rings that make up inner and outer housings. While the upper end of the inner housing is open, the upper end of the outer housing is sealed with a microporous, hydrophobic membrane that allows gases to pass through but does not allow liquids to pass. A gap is maintained between the open upper end of the inner housing and the membrane. The annular concentric housings define an inner first chamber and an outer second chamber. During dialysis, dialysate mixed with carbon-dioxide enters into and moves up the outer second chamber causing carbon dioxide to be automatically separated from the dialysate thereby forming small carbon dioxide bubbles that are vented out through the microporous hydrophobic membrane, while the dialysate overflows into the inner first chamber and moves out of the degassing device.

In one embodiment, the present invention is directed to a degassing device comprising a) a first housing having an inlet, a first length and an inner wall defining a first inner chamber, b) a second housing positioned within said first inner chamber in an annular relation to the first housing wherein the second housing has an outer wall, an outlet, a second length and an inner wall defining a second inner chamber, wherein the second length is less than the first length, and wherein a space between the first length and second length defines a gap, c) a flowpath through said degassing device wherein said flowpath is defined by the inlet, the gap, and the outlet, and d) a hydrophobic membrane positioned proximate to said gap.

Optionally, the degassing device has a gap between about 0.02 inches and 0.1 inches, has a space between said inner wall of the first housing and outer wall of the second housing between about 0.04 to 0.24 inches, and is capable of removing substantially all gas from dialysate at flow rates between 20 ml/min and 450 ml/min. Optionally, the second housing comprises a filter, the filter is approximately 0.1 to 0.4 inches thick, and the hydrophobic membrane is positioned a distance from the second housing wherein the distance is equal to the gap.

Optionally, the inlet and outlet are positioned on a same side of said degassing device. Fluid having gas flows into the first inner chamber through said inlet, flows through said gap, flows past the hydrophobic membrane, flows into said second inner chamber, and flows through said outlet, wherein gas passes through the hydrophobic membrane and wherein liquid does not pass through said hydrophobic membrane. Optionally, a dialysate circuit comprises a dialysate regeneration system with urease, a dialyzer, and this degassing device, which is positioned between the urease and the dialyzer.

In another embodiment, the present invention is directed to a dialysate circuit comprising a) a dialysate regeneration system comprising urease, b) a housing comprising an external wall, wherein the external wall is exposed to atmosphere and wherein the external wall comprises a material that passes gas but does not pass liquid, and c) a dialyzer, wherein said tube is positioned between the urease and dialyzer. The housing preferably is just a tube a section of tubing, or a coil of tubing with nothing internal to the tube (the inner chamber defined by the external walls is devoid of any structures or obstructions) and with the external wall exposed to atmosphere, or at least to an area external to the degassing device.

Optionally, the dialysate circuit comprises a membrane that is between 0.5 feet to 16 feet long, has an outer diameter of about 0.1 to 0.45 inches, or has an inner diameter of about 0.1 to 0.4 inches. Optionally, the housing (degassing device) removes substantially all gas from the dialysate at flow rates from about 20 ml/min to 200 ml/min or at internal pressures at or below 10 psi. Optionally, the dialysate regeneration system comprises charcoal and the housing is positioned between the charcoal and dialyzer.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1:
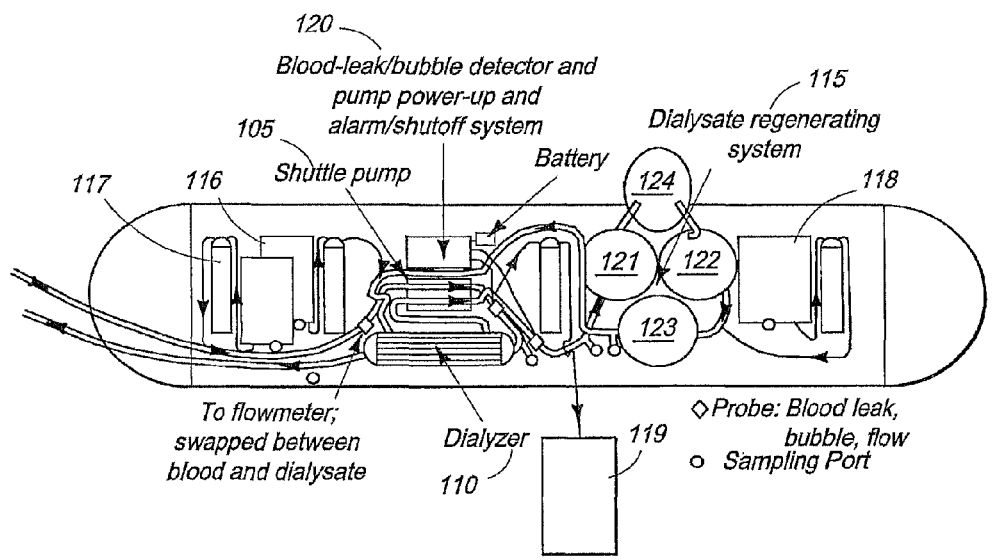
FIG. 1 is a schematic illustration of an embodiment of an exemplary wearable dialysis system.

While the present invention may be embodied in many different forms, for the purpose of promoting an understanding of the invention, reference will now be made to the embodiments illustrated in the drawings and specific language will be used to describe the same. It will nevertheless be understood that no limitation of the scope of the invention is thereby intended. The present specification incorporates by reference co-pending, co-assigned U.S. patent application Ser. Nos. 12/324,924, 12/210,080, 12/238,055, 12/237,914, 12/249,090, and 12/245,397 and third party owned U.S. Pat. No. 6,960,179, U.S. patent application Ser. Nos. 10/940,862, 10/846,618, 11/427,267, 11/500,572 and PCT Application No. PCT/US06/30923.

Closed loop multi-pass sorbent based dialysis systems regenerate dialysate for reuse by passing spent dialysate through a regeneration section comprising a plurality of sorbent cartridges and suitable additives. A typical sorbent cartridge system comprises a urease cartridge, a zirconium phosphate cartridge, a hydrous zirconium oxide cartridge and an activated carbon cartridge. Those of ordinary skill in the art will recognize that these sorbents are similar to the sorbents employed by the commercially available REDY™ System.

As spent dialysate passes through the REDY™ sorbent system the conversion of urea to ammonium carbonate, the exchange of ammonium ions for hydrogen ions, and the reaction of the hydrogen ions with carbonate in the sorbent system, produces substantial amounts of carbon dioxide. These large amounts of carbon dioxide that leave the liquid phase and the ensuing bubbles interfere with smooth pumping of dialysate and therefore need to be removed from the system. In addition, other gases may leave the liquid phase and, together with the carbon dioxide, presents bubbles that need to be removed.

Accordingly, the present invention is a degassing device that functions to remove carbon dioxide or any other gas from closed circuit dialysis systems. The degassing device of the present invention is suitable for functioning in any orientation apart from being small in size and low cost enough to be disposable thus eliminating the need for periodic cleaning and sterilization.

Figure 4:
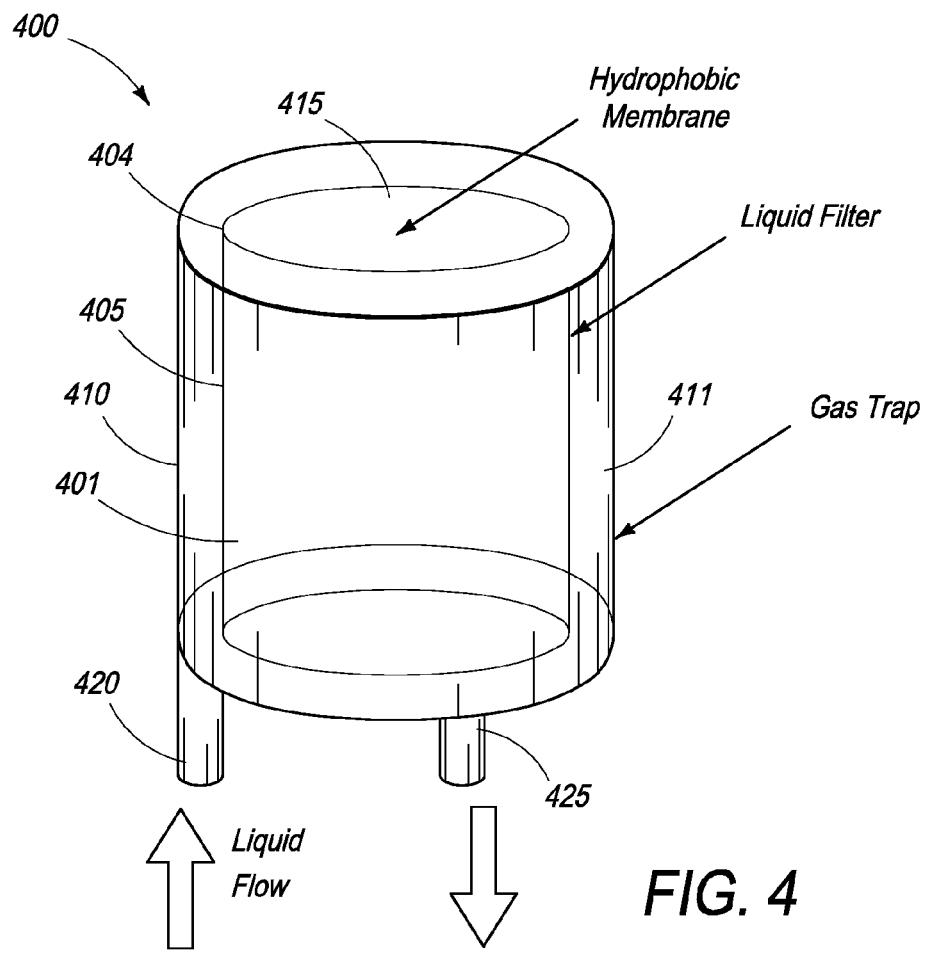
FIG. 4 is a diagram depicting another exemplary embodiment of the degassing device of the present invention.

FIG. 4 shows one embodiment of the degassing device 400 of the present invention comprising two annular cylindrical housings 405, 410. The housings 405, 410 are concentric. The upper end of the inner housing 405 is open and forms a circular rim 404. The upper end of the outer housing 410 is sealed with a microporous, hydrophobic membrane 415 that allows gases to pass through but does not allow liquids to pass. The hydrophobic membrane can be of any suitable type, including a PALL™ hydrophobic membrane, a Gore™ hydrophobic membrane, including model numbers SMPL-MMT317, MMT-RD-001, MMT-RD-002B and MMT-RD-002A. A gap exists between the upper end of the inner housing 405 and the hydrophobic membrane sealed upper end of the outer housing 410. The gap is sized to allow gas bubble passage within the gap. Typical dimensions from 0.002" to 0.025", and more particularly from 0.05" to 0.15", have been used in the preferred embodiment. The inner housing 405 defines an inner first chamber 401 while the concentric region between the inner and the outer housings 405, 410 constitutes a second chamber 411. An inlet tube 420 is connected to an inlet orifice at the second chamber 411 while an outlet tube 425 is connected to an outlet orifice at the first chamber 401.

In one embodiment, the inner first housing 405 has a discontinuous internal surface to provide areas upon which gas within the liquid can nucleate, collect, form bubbles, and migrate up and through the top hydrophobic membrane. In one embodiment, the inner first housing comprises a filter membrane which is approximately 0.1 to 0.4 inches thick (more particularly 0.25 inches), has an inner diameter of 0.5 to 1.5 inches (more particularly 1 inch), and an outer diameter of 0.5 inches to 2.5 inches (more particularly 1.5 inches). In another embodiment, the gap at the top, between the inner first housing 405 and hydrophobic membrane 415 is about 0.02 to 0.1 inches (more particularly 0.064), the gap between the outside of the inner first housing 405 and the inner wall of the outer housing 410 is about 0.04 to 0.24 inches (more particularly 0.141 inches), and there is no gap between the inner first housing 405 and the base of the degassing device 400. In one embodiment, the degassing device 400 has a height of 1 to 5 inches (more particularly three inches) and an outer diameter of 0.5 to 3 inches (and more particularly 1.75 inches). The degassing device is able to substantially remove all gas from the dialysate at a flow of 20 ml/min to 450 ml/min (more particularly 250 ml/min).

During hemodialysis, dialysate mixed with carbon dioxide enters the inlet tube 420 and passes into the concentric second chamber 411, overflows into the inner first chamber 401 through the gap and flows out the outlet tube 425 connected to the first chamber 401. During this process as the dialysate and carbon dioxide mixture is fed through the inlet tube 420, the mixture moves upwards causing carbon dioxide to be separated from the dialysate thereby forming small carbon dioxide bubbles that are vented out through the microporous hydrophobic membrane 415. The dialysate-free carbon dioxide moves through and out the outlet tube 425. The degassing chamber can be placed at various locations in the dialysis flow, but preferably in the flow stream immediately after the dialysate is subjected to filtration in sorbent canisters, depicted as 520 in FIGS. 5a and 5b. It should be appreciated that, regardless of where the degassing chamber is placed in the system, it should be vertically maintained, with membrane 415 at the top of the device, in order to properly direct air bubbles through and out of the device 400.

FIG. 1 shows a closed multi-pass hemodialyzer configured as a wearable dialysis device 100 that, in one embodiment comprises a shuttle pump or dual-channel pulsatile pump 105 to propel both blood and dialysate through the device 100, a high flux, polysulfone dialyzer 110 with 0.6 square meter membrane surface, a dialysate regeneration system 115 consisting of three specially designed canisters containing a plurality of sorbents, such as 122, zirconium, phosphate, 123, activated charcoal, and 121 urease, as well as reservoirs of electrolyte additives 116 and a pH-control circuit (not shown); micro-pumps (not shown) for delivering heparin 117 to the blood circuit, additives including Mg, Ca, K and sodium bicarbonate 118, and a reservoir for excess ultrafiltrate 119, all at pre-specified flow rates; and a blood-leak/bubble detector and pump power-up and alarm/shutoff system 120.

The main pump 105 uses a 3-Watt DC micro motor. The gear-head accommodates an oscillating mechanism, which in conjunction with a dual-channel flow cartridge, allows simultaneous pulsatile flows of both blood and the dialysate at controllable rates of 40-100 ml/min per channel. The cartridge allows both blood and dialysate to flow either in the same direction or in opposite directions, depending on the configuration/location of the other system components. It is preferred, however, that, when one channel propels fluid out of its compressible chamber, the other channel fills its compressible chamber, allowing for peak pressure in one channel at the same time the pressure in the other channel is at its lowest level.

In one embodiment, the sorbent canisters of the present invention are filled (in order of dialysate flow) with approximately the following amounts of sorbents:

121, Canister #1: 50 grams of urease, followed by thin filter paper, and then 335 grams of zirconium phosphate;

122, Canister #2: 335 grams of zirconium phosphate, followed by thin filter paper, and then 50 grams of hydrous zirconium oxide; and 123, Canister #3: 150 grams of activated carbon.

Figure 5A:
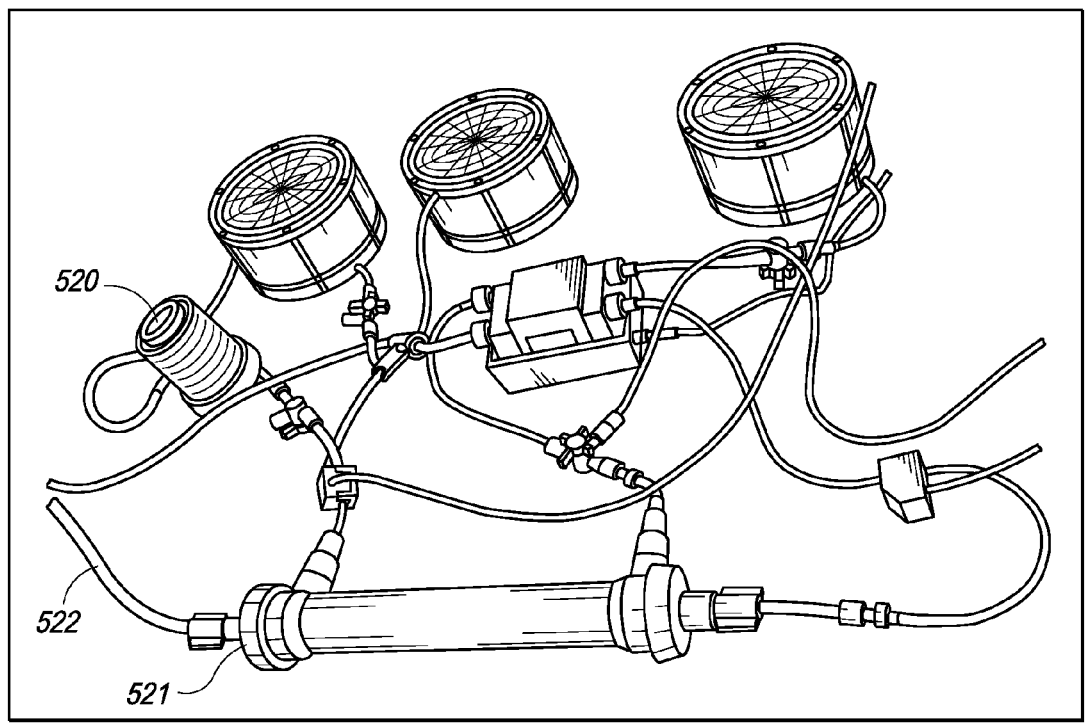
FIG. 5a depicts a scaled up degassing device in relation to a dialyzer.

Degassing device 124 is located in the fluidic circuit between urease canister 121, and Zirconium Phosphate canister 122. Carbon dioxide gas generated by the urease-urea reaction in canister 121 is removed by the degassing device 124, before the dialysate fluid is passed into canister 122. Other positioning of the degassing device, within the circuit, is possible, in particular after all the sorbent canisters, following the charcoal canister, 123 as shown in FIG. 5a. It should be appreciated that the degassing device 124 could be located after canister 122 and before canister 123 or after canister 123 and before dialyzer 110.

Figure 5B:
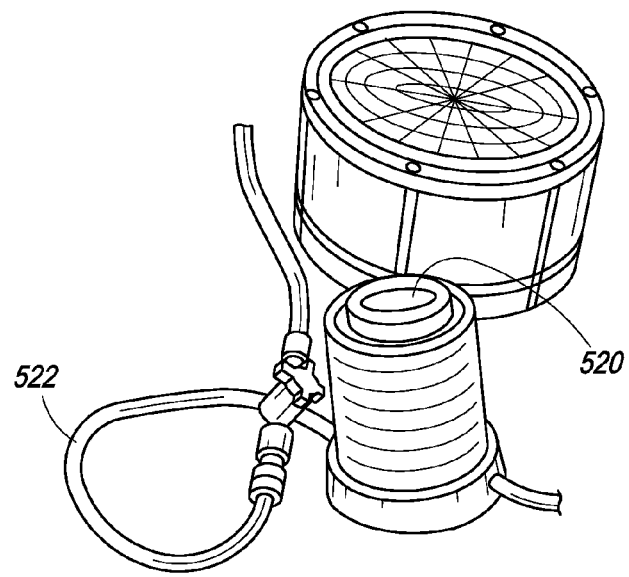
FIG. 5b depicts another view of a degassing device comprising material that passes gas but not liquid.

Another embodiment of the degassing device 124 is shown in FIGS. 5a and 5b. The device 520 consists of a coil of gas permeable tubing, such as that manufactured by GORE, Inc., tubing part number MMT-RD-002A. In FIG. 5a, the degassing device 520 is connected, via tubing 522, to a dialyzer. FIG. 5b depicts the degassing device 520 connected to tubing 522. This tube is 9 feet long, has an outside diameter of approximately 0.275" and a wall thickness of approximately 0.025". The coil assembly is approximately 2.25" outside diameter and approximately 2.5" in height. In this embodiment, the entire outer wall of the outside chamber is gas permeable. Because gas can now diffuse through any portion of the outer wall, not just the top as in the embodiment disclosed in FIG. 4, the device can be placed in nearly any orientation, making it well suited for use with a wearable dialysis system such as that depicted in FIG. 1. In one embodiment of the device the total tube length is 9 feet. This size is designed to yield an adequate surface area to provide gas removal capability for a typical wearable artificial kidney operating around the 24 hours a day, seven days a week with a dialysate and blood flow rate at or below 100 ml/min. Shorter lengths of tubing (therefore possessing lower surface area) can be used for removing less gas, such as if flow rates were lowered or longer lengths can be used for increased gas removal capacity.

In operation, gas collects in a self generated pocket on the top of the many coils of the gas permeable tubing in device 520. This location of the gas pocket changes depending on the orientation of the device. Gravity dictating that the gas collects on whatever surface is "up" in varying orientations. Since the entire length of the device is composed of gas permeable tubing, no matter where the gas pocket collects it is able to escape.

Alternate packaging of the tube may include long serpentine shaped runs accommodating the shape of a belt worn around the waist of a patient using a wearable artificial kidney. Thus the embodiment pictured in FIG. 5b is not exclusive to the functionality of the degassing device. The key factor is that whatever shape the device takes the fluid path be composed of a gas permeable tube of sufficient length, and therefore surface area, to remove the amount of gas desired.

Figure 3:
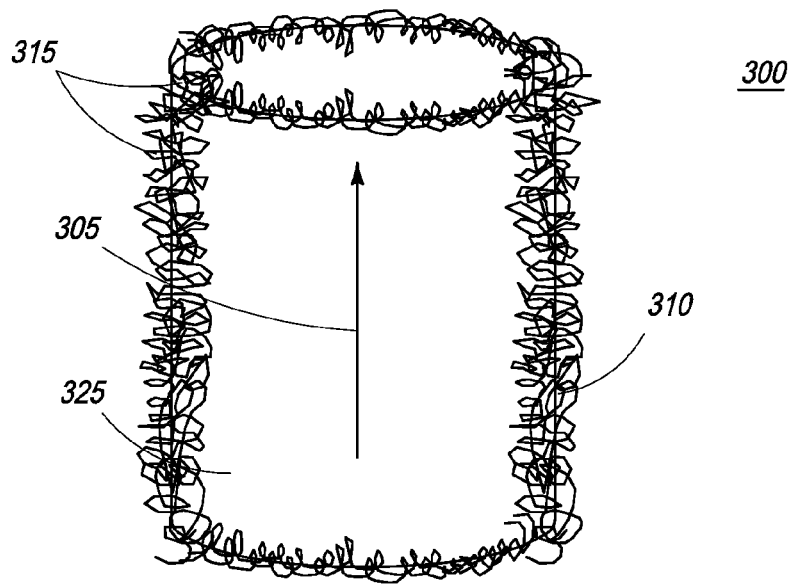
FIG. 3 is a diagram depicting an exemplary embodiment of the degassing device of the present invention.

In another embodiment, shown in FIG. 3, the degassing device 300 is a section of a tube, a housing, a coil of tubing, or any other shape 310 that defines a chamber 325 and a flowpath 305 therein. The external wall of the housing 310 comprises any material 315 that will pass gas but not fluid. The material 315 must be sized so that the amount of gas passed equals or exceeds the amount of gas generated. Gas generation is a product of urea level in the patient and dialysate flow rate. Gas passed by the degassing device 300 is a product of the wall area and the gas permeability of the tube plus the internal pressure of the fluid in the tube relative to the external pressure on the tube. One of ordinary skill in the art would be able to select the appropriate material for a given application based upon the given parameters.

In one embodiment, the degassing device comprises a GORE membrane that is between 0.5 feet to 16 feet long (more particularly 9 feet long), has an outer diameter of about 0.1 to 0.45 inches (more particularly 0.275 inches) and an inner diameter of about 0.1 to 0.4 inches (more particularly 0.25 inches) and configured in any shape, including a tight coil. In one embodiment, the aforementioned degassing device 300 removes substantially all gas from the dialysate at flow rates from about 20 ml/min to 200 ml/min (more particularly 100 ml/min) and/or at internal tube pressures at or below 10 psi (more particularly at or below 5 psi). In one embodiment, the degassing device 300 is positioned between a sorbent canister (more particularly the charcoal sorbent) and the dialyzer. In one embodiment, the degassing device 300 is positioned after the urease canister and before the dialyzer.

PERFORMANCE EXAMPLE 1

Figure 2:
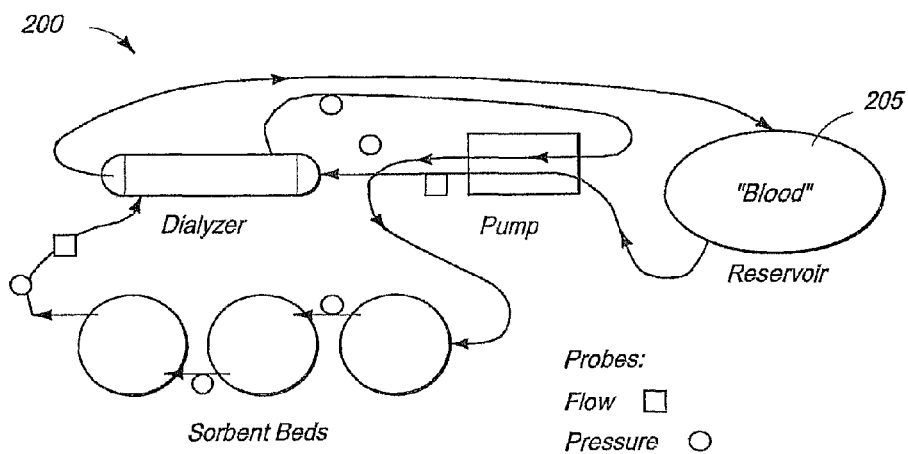
FIG. 2 is a schematic illustration of an exemplary process flow for performing dialysis.

Various configurations of the dialysis device 100 of FIG. 1 were tested to evaluate their operational performance and, in particular, the gas removal capability of the degassing device 124 and 520. Referring to FIG. 2, after priming the dialysis device with saline, the dialysis device 200 was connected to a large (40- to 80-liter) reservoir 205 of properly formulated aqueous solution (referred to as "blood" here, made out of fresh deionized water or spent human dialysate) accurately mimicking end stage renal disease (ESRD) typical human blood. This "blood" was designed to approximate actual human composition and contained about 50 mg/dL of BUN (Blood Urea-Nitrogen), 10 mg/dL of creatinine, 5 mmol/L of K, among other solutes. No additives were provided and no ultrafiltration was performed; however, dialysate pH was maintained at an optimal value by a manual injection of sodium bicarbonate in order to measure its effect on the volume of $CO_2$ produced. "Blood" and dialysate samples were drawn every 30 minutes, and the samples were assayed for pH, BUN, and creatinine.

In one experiment, which used a Gore tube MMT-RD-002A, to fabricate degassing device 520, sorbent canisters were packed with 50 grams of urease, 670 grams of zirconium phosphate, 50 grams of hydrous zirconium oxide, and 150 grams of activated carbon, and operated at an average blood and dialysate flow rates of 55.6 and 43.2 mL/min, pressure reading oscillating ranges were measured to be: a) between pump and canister #1: 300-400 mmHg, b) between canisters #1 and #2: 150-220 mmHg, c) between canisters #2 and #3: 55-65 mmHg; and d) between dialyzer and pump: 2-35 mmHg (rarely going below 0). The urea, measured as BUN (Blood Urea-Nitrogen) when reacted with the Urease generated $CO_2$ in amounts dictated by the flowrate and urea concentrations present. Such conditions were set up to mimic actual human dialysis. Under these test conditions the degassing device successfully removed all the $CO_2$ generated.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A degassing device comprising:
    a. a first housing having an inlet, a first length and an inner wall having an upper end, defining a first inner chamber;
    b. a second housing positioned within said first inner chamber in an annular, concentric relation to the first housing wherein the second housing has an outer wall, an outlet, a second length and an inner wall defining a second inner chamber, wherein the second length is less than the first length, and wherein a space between the first length and second length defines a gap;
    c. a flowpath through said degassing device wherein said flowpath is defined by the inlet, the gap, and the outlet; and
    d. a hydrophobic membrane positioned proximate to said gap and over the upper end of the first housing.

2. The degassing device of claim 1 wherein the gap is between about 0.02 inches and 0.1 inches.

3. The degassing device of claim 1 wherein a space between said inner wall of the first housing and outer wall of the second housing is between about 0.04 to 0.24 inches.

4. The degassing device of claim 1 wherein said degassing device is capable of removing substantially all gas from dialysate at flow rates between 20 ml/min and 450 ml/min.

5. The degassing device of claim 1 wherein said second housing comprises a filter.

6. The degassing device of claim 5 wherein the filter is approximately 0.1 to 0.4 inches thick.

7. The degassing device of claim 1 wherein the hydrophobic membrane is positioned a distance from said second housing wherein said distance is equal to the gap.

8. The degassing device of claim 1 wherein the inlet and outlet are positioned on a same side of said degassing device.

9. The degassing device of claim 1 wherein fluid having gas flows into the first inner chamber through said inlet, flows through said gap, flows past the hydrophobic membrane, flows into said second inner chamber, and flows through said outlet, wherein gas passes through the hydrophobic membrane and wherein liquid does not pass through said hydrophobic membrane.

10. A dialysate circuit comprising a dialysate regeneration system with urease, a dialyzer, and the degassing device of claim 1.

11. The dialysate circuit of claim 10 wherein said degassing device is positioned between the urease and the dialyzer.

* * * * *